(12) United States Patent
Sharma

(10) Patent No.: US 11,707,628 B2
(45) Date of Patent: Jul. 25, 2023

(54) RATE RESPONSIVE PACING

(71) Applicant: Medtronic, Inc., Minneapolis, MN (US)

(72) Inventor: Vinod Sharma, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 52 days.

(21) Appl. No.: 16/878,740

(22) Filed: May 20, 2020

(65) Prior Publication Data

US 2020/0376279 A1 Dec. 3, 2020

Related U.S. Application Data

(60) Provisional application No. 62/854,703, filed on May 30, 2019.

(51) Int. Cl.
| | |
|---|---|
| *A61N 1/00* | (2006.01) |
| *A61N 1/365* | (2006.01) |
| *A61N 1/05* | (2006.01) |
| *A61N 1/368* | (2006.01) |

(52) U.S. Cl.
CPC ....... *A61N 1/36542* (2013.01); *A61N 1/3655* (2013.01); *A61N 1/36507* (2013.01); *A61N 1/36521* (2013.01); *A61N 1/36564* (2013.01); *A61N 1/36571* (2013.01); *A61N 1/36578* (2013.01); *A61N 1/36585* (2013.01); *A61N 1/056* (2013.01); *A61N 1/3684* (2013.01)

(58) Field of Classification Search
None
See application file for complete search history.

(56) References Cited

U.S. PATENT DOCUMENTS

| | | | |
|---|---|---|---|
| 4,884,576 A | 12/1989 | Alt | |
| 5,040,534 A | 8/1991 | Mann et al. | |
| 5,282,839 A * | 2/1994 | Roline | A61N 1/36585 607/19 |
| 5,423,870 A * | 6/1995 | Olive | A61N 1/36585 607/18 |
| 5,609,613 A * | 3/1997 | Woodson | A61N 1/3622 607/19 |
| 5,720,769 A | 2/1998 | van Oort et al. | |
| 5,807,234 A | 9/1998 | Bui et al. | |
| 6,129,744 A | 10/2000 | Boute | |
| 6,836,682 B2 | 12/2004 | Van Dam | |
| 9,724,518 B2 * | 8/2017 | Sheldon | A61N 1/36585 |
| 9,937,352 B2 | 4/2018 | Sheldon et al. | |

(Continued)

OTHER PUBLICATIONS (PCT/US2020/034474) PCT Notification of Transmittal of the International Search Report and the Written Opinion of the International Searching Authority, dated Aug. 25, 2020, 9 pages.

*Primary Examiner* — John R Downey
*Assistant Examiner* — Anant A Gupta
(74) *Attorney, Agent, or Firm* — Mueting Raasch Group

(57) ABSTRACT

Some aspects relate to systems, devices, and methods of delivering rate responsive pacing therapy. The method includes monitoring activity information related to an activity level of a patient and delivering rate responsive pacing (RRP) to the patient at a pacing rate corresponding to a RRP profile. The RRP profile may be used to generate the pacing rate based on the activity information and may be adjusted based on the monitored activity information.

16 Claims, 9 Drawing Sheets

(56) References Cited

U.S. PATENT DOCUMENTS

| | | |
|---|---|---|
| 2003/0120319 A1 | 6/2003 | Sun et al. |
| 2007/0150015 A1* | 6/2007 | Zhang ................ A61N 1/39622 |
| | | 607/17 |
| 2011/0029034 A1 | 2/2011 | Fischer et al. |
| 2013/0138171 A1* | 5/2013 | Wahlberg ........... A61N 1/36514 |
| | | 607/19 |
| 2013/0150912 A1 | 6/2013 | Perschbacher et al. |

* cited by examiner

RATE RESPONSIVE PACING

This disclosure generally relates to cardiac pacing methods and systems, and more particularly, to methods and systems for delivering rate responsive pacing with an implantable medical device.

Heart failure (HF) is a complex disease that is broadly defined by an inability of the heart to pump sufficiently to cope with its venous return and/or to deliver sufficient output to meet the metabolic demands of the body. Heart failure is an increasingly common, life-threatening cardiovascular disorder, characterized by marked disability, frequent hospitalization, and high mortality. HF is increasingly prevalent in older individuals (up to 10% of the population) and it has become the most common cause for hospitalization in people >65 yrs. HF is a leading cause or contributor to hospitalization, and therefore, is emerging as a substantial contributor to healthcare spending.

Congestive heart failure symptoms (e.g., indicative of congestive heart failure) may include reduced cardiac output leading to easy fatigue and organ dysfunction (e.g. renal), and to symptoms related to congestion either in the lungs (causing breathlessness) or peripherally (leading to swelling of the lower limbs and abdomen).

A possible correlation has been identified between sedentary lifestyle and risk of ventricular arrhythmias based on a comparison of occurrences of ventricular arrhythmias in healthy active vs. sedentary patients, and patients with previous myocardial infarction. One result of a sedentary lifestyle is that the size of the chambers of the heart may decrease, which often occurs as a result of increased muscle thickness. The reduced chamber size leads to decreased stroke volume (SV, amount of blood ejected with each heart beat), even though the fraction of blood (ejection fraction) ejected with each beat is preserved. Reduced stoke volume per beat leads to reduced cardiac output (CO, CO=SV*heart rate (HR)). Cardiac output is typically measured in liters of blood pumped per minute by heart. A reduced cardiac output may mean that the body's metabolic demand, especially during periods of ambulation or exercise is not met. This leads to heart failure symptoms such as dyspnea (shortness of breath) with activities of daily living (ADL). This type of heart failure in which ejection fraction (EF) is preserved is referred to as heart failure with preserved ejection fraction (HFpEF). From the relationship between CO=SV*HR, it can be seen that one way to increase cardiac output and meet the body's demand during periods of ambulation, activities of daily living, and exercise is to increase the HR appropriately.

In congestive heart failure patients with HFpEF the amount of blood pumped from the heart's left ventricle with each beat (ejection fraction) is greater than 50%. HFpEF is also commonly known as diastolic heart failure or diastolic dysfunction, as the deficit in function frequently relates to changes occurring during diastole and filling of the ventricles. Approximately half of people with heart failure have HFpEF, while the remainder display a reduction in ejection fraction, or heart failure with reduced ejection fraction (HFrEF).

The prevalence of HFpEF continues to increase, likely because of the increasing prevalence of common risk factors, including older age, hypertension, metabolic syndrome, renal dysfunction and obesity. HFpEF is characterized by abnormal diastolic function, which manifests as an increase in the stiffness of the heart's left ventricle, a decrease in left ventricular relaxation when filling with blood before the next beat, and decreased chamber volume, which often occurs as a result of increased muscle thickness. There is an increased risk for atrial fibrillation and pulmonary hypertension for patient's experiencing HFpEF.

Chronotropic incompetence (CI) is common among HFpEF patients and is characterized by decreased heart rate response during activities of daily living or other activities requiring increase in cardiac output (e.g., exercise). HFpEF patients with CI often cannot elevate their sinus/atrial rate. Maximum exercise and peak heart rate achieved during exercise are both decreased in a patient with CI.

Cardiac pacing is delivered according to a pacing rate. The pacing rate may be described as the rate at which the heart is paced thereby increasing or decreasing the patient's heart rate. The pacing rate may be defined in terms of beats per minute. In some examples, the pacing rate may be defined in terms of R-R interval that is the time between successive heartbeats. Rate responsive pacing can adapt the pacing rate to changes in the patient's physical activity. Rate responsive pacing can be useful to allow the heart rate to increase with increased metabolic demand, such as during activities of daily living and exercise, for example.

SUMMARY

The techniques of this disclosure generally relate to a method and device for delivering a rate responsive pacing therapy to a patient's heart over a period of time.

Some aspects, in accordance with principles of the present disclosure, relate to a method including monitoring activity information related to an activity level of a patient, delivering rate responsive pacing (RRP) to the patient at a pacing rate corresponding to a RRP profile, wherein the RRP profile generates the pacing rate based on the activity information, and adjusting the RRP profile based on the monitored activity information.

Other aspects, in accordance with principles of the present disclosure, relate to an implantable medical device including a sensing apparatus, a control apparatus, and an electrode apparatus. The sensing apparatus may include one or more sensors to sense activity information of a patient. The control apparatus includes processing circuitry to select a rate responsive pacing (RRP) profile based on the sensed activity information received from the sensing apparatus. The electrode apparatus includes a plurality of pacing electrodes, the electrode apparatus operably coupled to the control apparatus. The electrode apparatus delivers rate responsive pacing (RRP) to the patient at a pacing rate corresponding to the RRP profile. The RRP profile is adjustable based on the sensed activity information.

Other aspects, in accordance with principles of the present disclosure, relate to a rate responsive pacing system including a sensing apparatus, a control apparatus, and an implantable medical device. The sensing apparatus may include one or more sensors to sense activity information of a patient. The control apparatus includes processing circuitry. The control apparatus is operably coupled to the sensing apparatus and is configured to monitor sensed activity information of the patient, determine a first activity information of a patient related to a first activity level of the patient, and determine a second activity information related to a second activity level of the patient, compare the first activity information to the second activity information, and determine a rate responsive pacing (RRP) profile based on the compared activity information. The implantable medical device includes pacing electrodes and may be operably coupled to the control apparatus. The electrodes deliver rate responsive pacing (RRP) to the patient at a pacing rate corresponding to the determined RRP profile.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or apparatus for purposes of clarity, it should be understood that the techniques of this disclosure may be performed by a combination of units or apparatuses associated with, for example, an implantable medical device.

Illustrative cardiac therapy systems and devices may be further described herein with reference to FIGS. 1-3B that may utilize the illustrative systems, methods, and processes described herein with respect to FIGS. 4-7.

Figure 1:
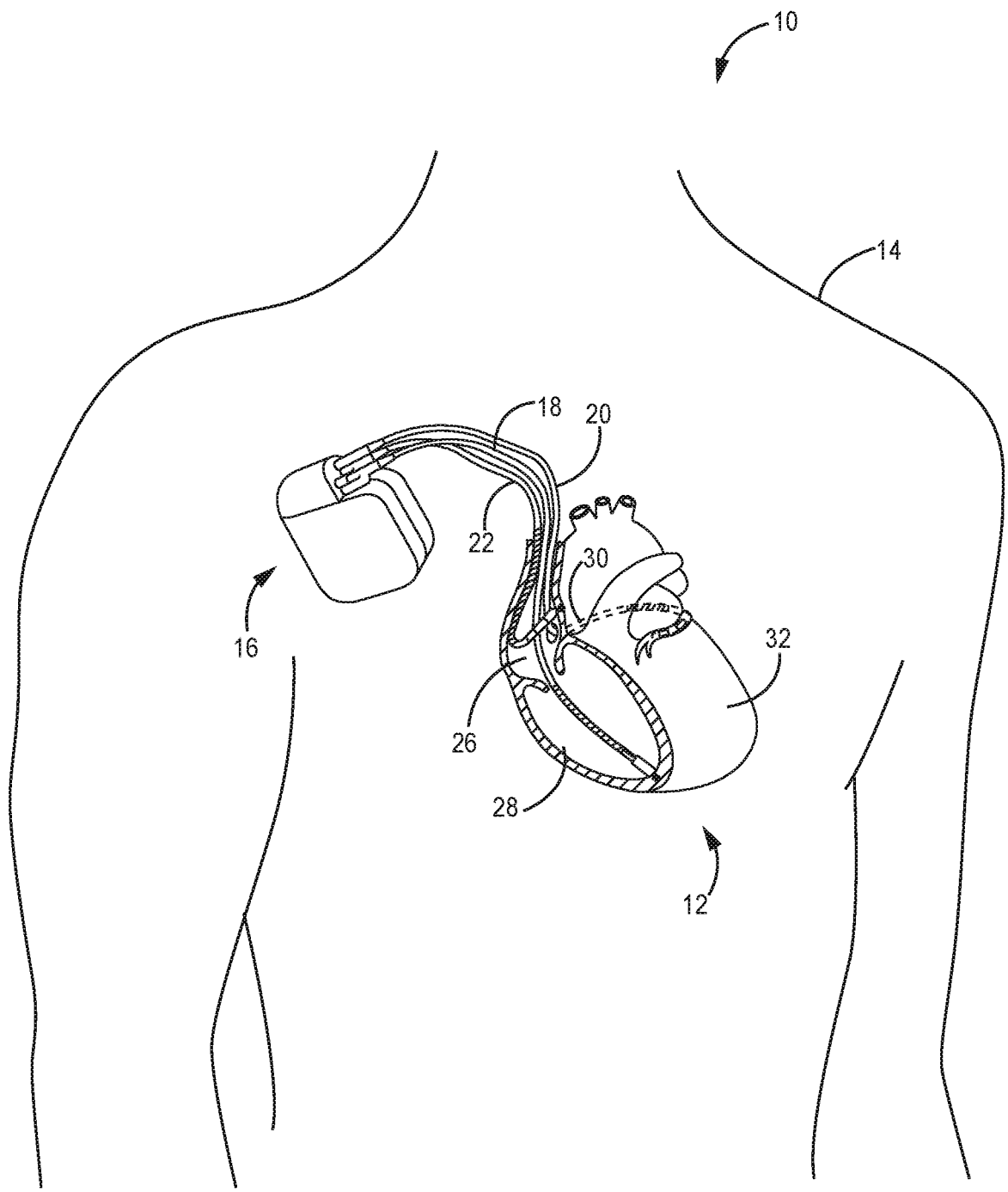
FIG. 1 is a diagram of an illustrative system including an illustrative implantable medical device (IMD).

FIG. 1 is a conceptual diagram illustrating an illustrative therapy system 10 that may be used to deliver pacing therapy, such as cardiac rate responsive pacing (RRP) to a patient 14. Patient 14 may, but not necessarily, be a human. The therapy system 10 may include an implantable medical device 16 (IMD), which may be coupled to leads 18, 20, 22. The IMD 16 may be, e.g., an implantable pacemaker, cardioverter, and/or defibrillator, that delivers, or provides, electrical signals (e.g., paces, etc.) to and/or senses electrical signals from the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The right atrial (RA) lead 22 extends through one or more veins and the vena cava, and into the right atrium 26 of the heart 12

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., pacing rate, R-R interval, A-V delay and other various timings, pulse wide, amplitude, voltage, burst length, etc. Further, the IMD 16 may be operable to use various electrode configurations to deliver pacing therapy, which may be unipolar, bipolar, quadripolar, or further multipolar. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD, or electrode apparatus. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

Figure 2A:
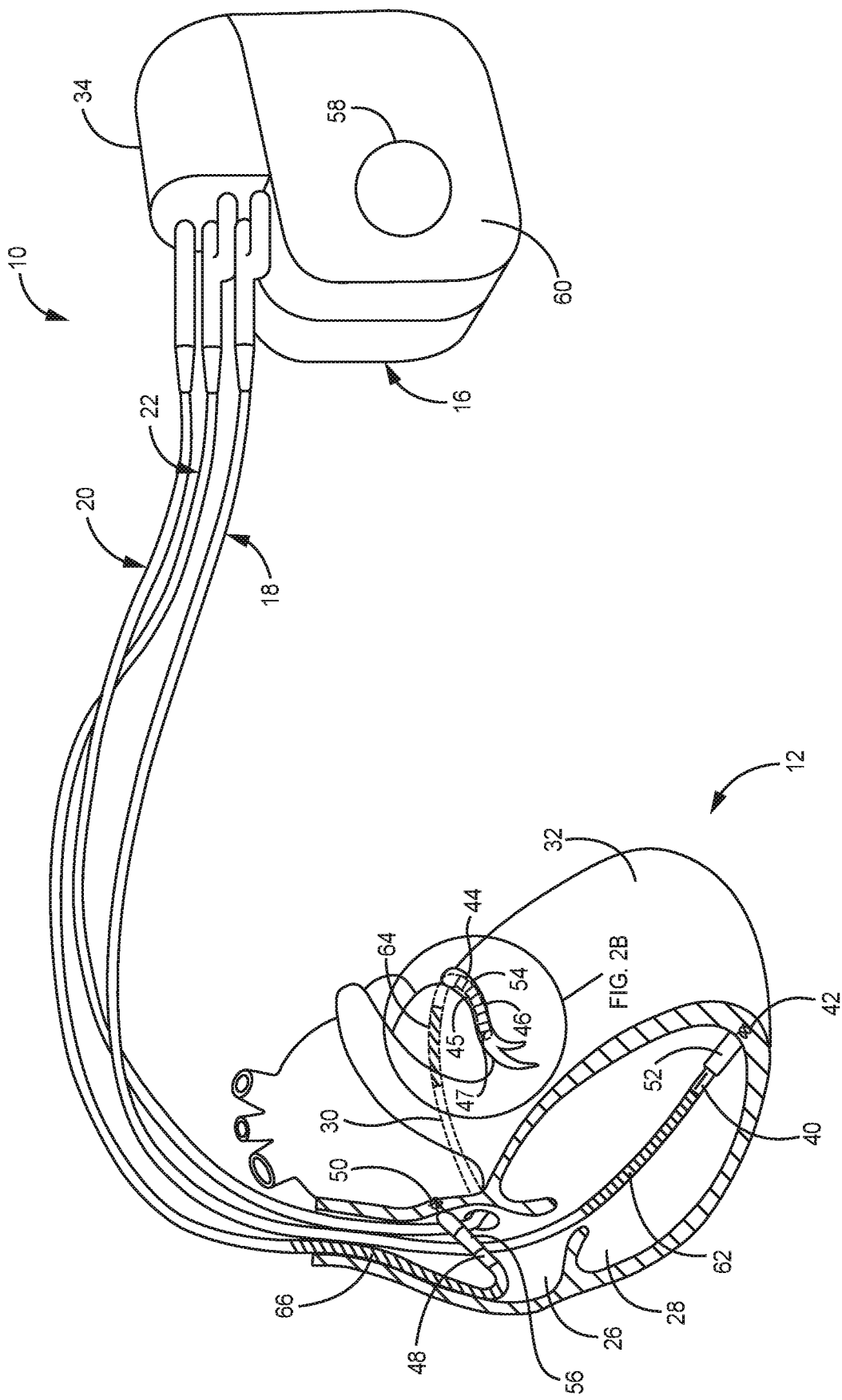
FIG. 2A is a diagram of the illustrative IMD of FIG. 1.
Figure 2B:
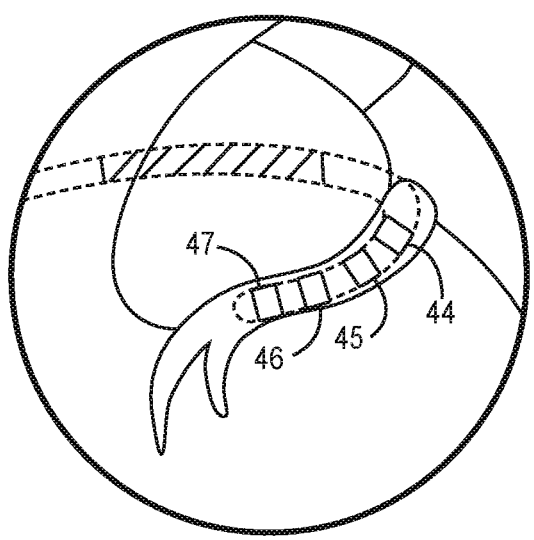
FIG. 2B is a diagram of an enlarged view of a distal end of the electrical lead disposed in the left ventricle of FIG. 2A

FIGS. 2A-2B are conceptual diagrams illustrating the IMD 16 and the leads 18, 20, 22 of therapy system 10 of FIG. 1 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, bipolar electrodes 44, 45, 46, 47 are located proximate to a distal end of the lead 20 and bipolar electrodes 48, 50 are located proximate to a distal end of the lead 22.

The electrodes 40, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to a respective one of the electrical contacts on the proximal end of the leads 18, 20, 22.

The electrodes 40, 42, 44, 45, 46, 47, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 2A, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48, 50 may be used for unipolar sensing or pacing in combination with the housing electrode 58. It is generally understood by those skilled in the art that other electrodes can also be selected to define, or be used for, pacing and sensing vectors. Further, any of electrodes 40, 42, 44, 45, 46, 47, 48, 50, 58, when not being used to deliver pacing therapy, may be used to sense electrical activity during pacing therapy.

As described in further detail with reference to FIG. 2A, the housing 60 may enclose a therapy delivery module that may include a stimulation generator for generating cardiac pacing pulses and defibrillation or cardioversion shocks, as well as a sensing module for monitoring the electrical signals of the patient's heart (e.g., the patient's heart rhythm). The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58, or defibrillation electrode-to-housing electrode vector).

The configuration of the illustrative therapy system 10 illustrated in FIGS. 1-3B is merely one example. In other examples, the therapy system may include epicardial leads and/or patch electrodes instead of or in addition to the transvenous leads 18, 20, 22 illustrated in FIG. 1. Additionally, in other examples, the therapy system 10 may be implanted in/around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 1). In one example, the left ventricular (LV) coronary sinus lead 20 extends through one or more veins, the vena cava, the right atrium 26, and into the coronary sinus 30 to a region adjacent to the free wall of the left ventricle 32 of the heart 12. Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 1-3B. Still further, other therapy systems may include a single lead that extends from the IMD 16 into the right atrium 26 or two leads that extend into a respective one of the right atrium 26 and the left atrium. In one example, the IMD 16, as a cardiac resynchronization therapy (CRT) device with a left ventricular (LV) lead may be useful for a HFpEF patient if there is a complete AV node block, as a LV lead can be more beneficial than a RV lead in such patients. In some examples, it can be desirable to deliver rate responsive pacing to the atrium for a HFpEF patient with CI with an atrial lead (i.e. single chamber atrial system such as AAI) and atrial and ventricular lead system (i.e. dual chamber system such as DDD and VDD).

Figure 3A:
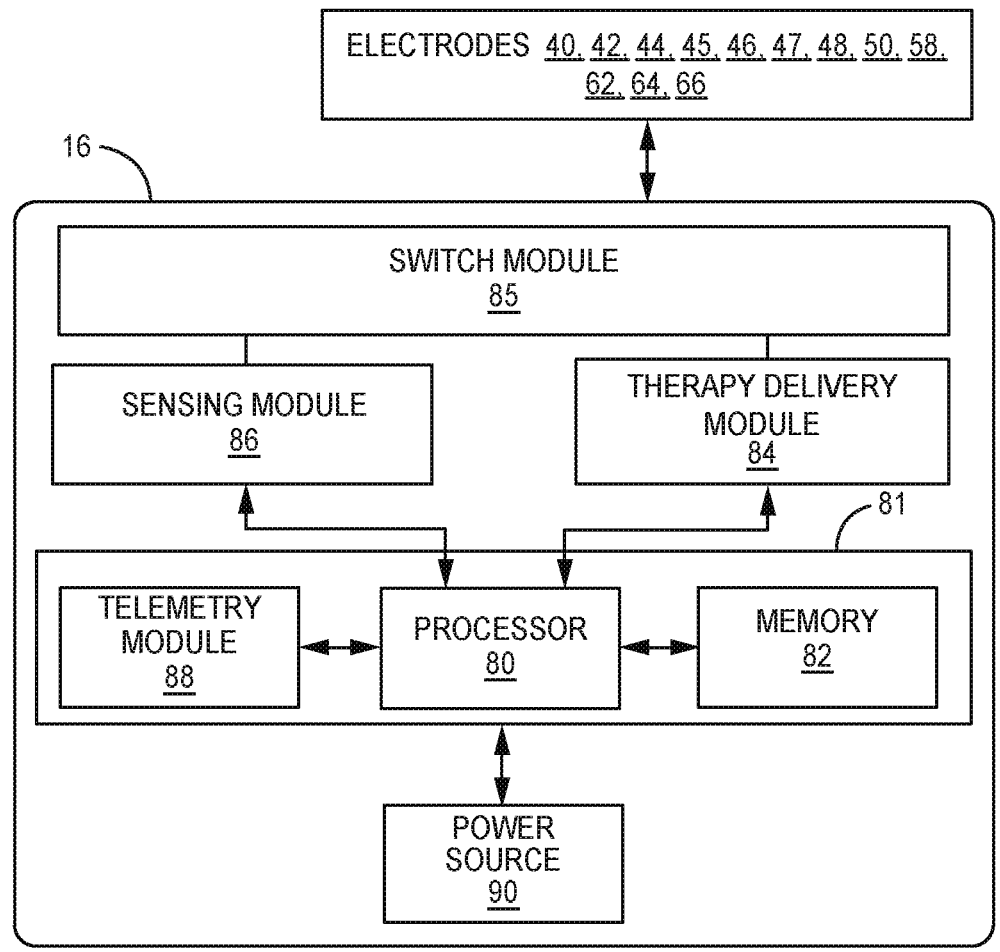
FIG. 3A is a block diagram of an illustrative IMD, e.g., of the systems of FIGS. 1-2B.

FIG. 3A is a functional block diagram of one illustrative configuration of the IMD 16. As shown, the IMD 16 may include a control module 81, a therapy delivery module 84 (e.g., which may include a stimulation generator), a sensing module 86, and a power source 90. The control module, or apparatus, 81 may include a processor 80, memory 82, and a telemetry module, or apparatus, 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random-access memory (RAM), read-only memory (ROM), non-volatile RAM (NVRAM), electrically-erasable programmable ROM (EEPROM), flash memory, and/or any other digital media.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module, or apparatus, 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., A-V delays, pacing pulses with the amplitudes, pulse widths, frequency, or electrode polarities, etc., which may be specified by one or more selected therapy programs (e.g., A-V delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, the therapy delivery module 84 may deliver pacing stimulus (e.g., pacing pulses) via ring electrodes 40, 44, 45, 46, 47, 48 coupled to leads 18, 20, 22 and/or helical tip electrodes 42, 50 of leads 18, 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured to deliver one or more of these types of stimulation in the form of other signals, such as sine waves, square waves, and/or other substantially continuous time signals.

The IMD 16 may further include a switch module, or apparatus, 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module, or apparatus, 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a bipolar or multipolar pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt-driven device and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 3B:
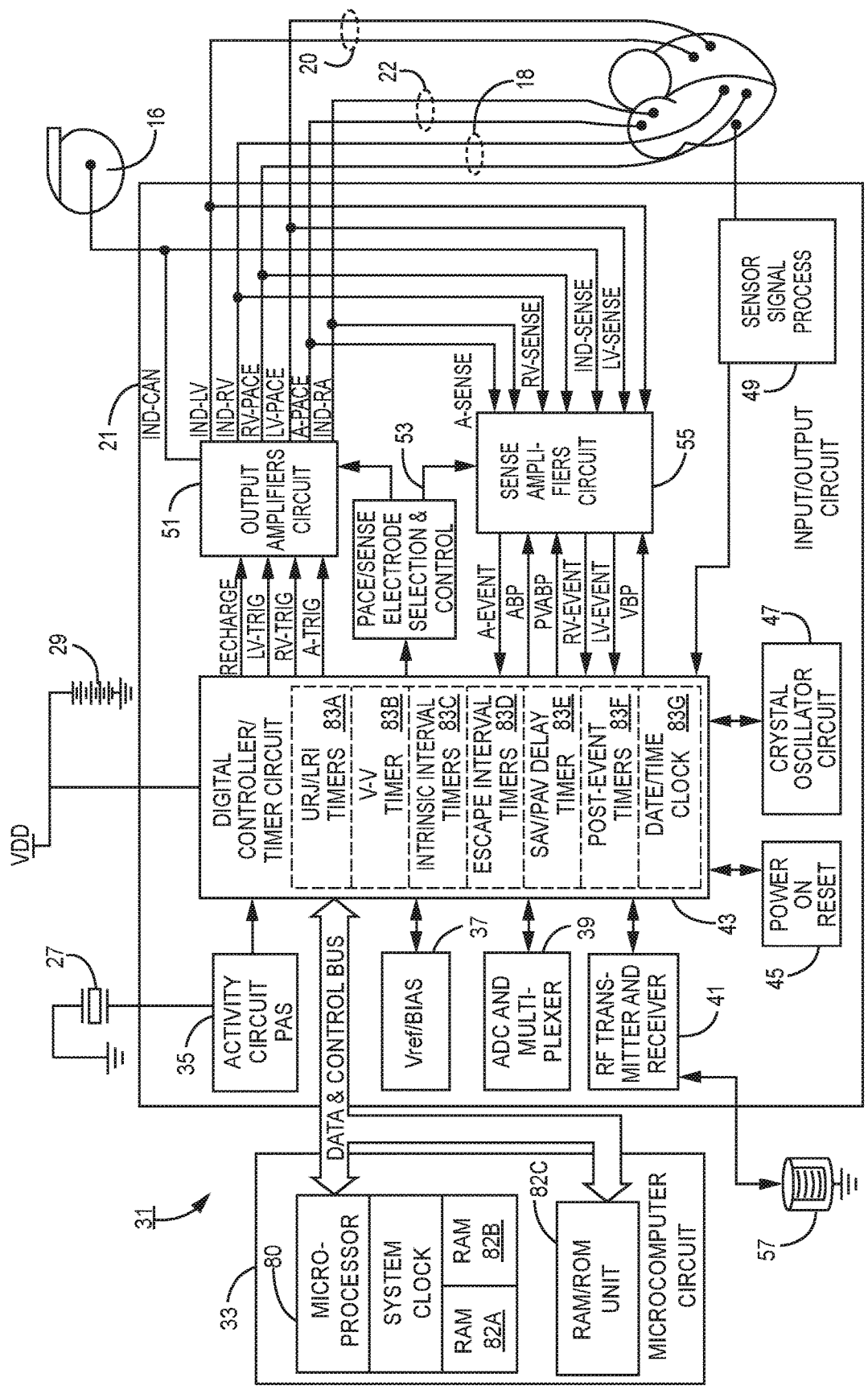
FIG. 3B is another block diagram of an illustrative IMD (e.g., an implantable pulse generator) circuitry and associated leads employed in the systems of FIGS. 1-2B.

FIG. 3B is another embodiment of a functional block diagram for IMD 16 that depicts bipolar RA lead 22, bipolar RV lead 18 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 43 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 43, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21 while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21. Analog-to-digital converter (ADC) and multiplexer circuit 39 digitize analog signals and voltage to provide, e.g., real time telemetry of cardiac signals from sense amplifiers 55 for uplink transmission via RF transmitter and receiver circuit 41. Voltage reference and bias circuit 37, ADC and multiplexer 39, power-on-reset circuit 87, and crystal oscillator circuit 89 may correspond to any of those used in illustrative implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally to the patient's activity level developed in the patient activity sensor (PAS) circuit 35 in the depicted, illustrative IPG circuit 31. The patient activity sensor 27 is coupled to the IPG housing and may take the form of a piezoelectric crystal transducer. The output signal of the patient activity sensor 27 may be processed and used as an RCP. Sensor 27 generates electrical signals in response to sensed physical activity that are processed by activity circuit 35 and provided to digital controller/timer circuit 43. Similarly, the illustrative systems, apparatus, and methods described herein may be practiced in conjunction with alternate types of sensors such as oxygenation sensors, pressure sensors, pH sensors, temperature sensors, respiration sensors, perfusion sensors, heart sound sensors, and heart rate sensors, for use in providing rate responsive pacing capabilities. For example, impedance can be measured using a ring electrode on the lead (e.g., RA or RV lead) and temperature can be measured by a sensor at the distal end of the lead. Alternately, QT time may be used as a rate indicating parameter, in which case no extra sensor is required. Similarly, the illustrative embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities may include the ability to transmit stored digital information, e.g., activity information, RRP profiles, operating modes and parameters, EGM histograms, and other events, as well as real time EGMs of atrial and/or ventricular electrical activity and marker channel pulses indicating the occurrence of sensed and paced depolarizations in the atrium and ventricle.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 43 and A-EVENT, RV-EVENT, and LV-EVENT signals generated by sense amplifiers circuit 55, among others. The specific values of the intervals and delays timed out by digital controller/timer circuit 43 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic pacing rate as well as A-A, V-A, as applicable. In addition, the microprocessor 80 may also serve to define variable, operative A-V delay intervals, and the energy delivered to each ventricle and/or atrium.

In one embodiment, microprocessor 80 is a custom microprocessor adapted to fetch and execute instructions stored in RAM/ROM unit 82 in a conventional manner. It is contemplated, however, that other implementations may be suitable to practice the present disclosure. For example, an off-the-shelf, commercially available microprocessor or microcontroller, or custom application-specific, hardwired logic, or state-machine type circuit may perform the functions of microprocessor 80.

Digital controller/timer circuit 43 operates under the general control of the microcomputer 33 to control timing and other functions within the pacing circuit 21 and includes a set of timing and associated logic circuits of which certain ones pertinent to the present disclosure are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals, escape interval timers 83D for timing A-A, and/or V-A pacing escape intervals, an A-V delay interval timer 83E for timing the A-LVp delay (or A-RVp delay) from a preceding A-EVENT or A-TRIG, a post-ventricular timer 83F for timing post-ventricular time periods, and a date/time clock 83G.

The A-V delay interval timer 83E is loaded with an appropriate delay interval for one ventricular chamber (e.g., either an A-RVp delay or an A-LVp) to time-out starting from a preceding A-PACE or A-EVENT. The interval timer 83E triggers pacing stimulus delivery and can be based on one or more prior cardiac cycles (or from a data set empirically derived for a given patient).

The post-event timer 83F times out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include a post-ventricular atrial blanking period (PVARP), a post-atrial ventricular blanking period (PAVBP), a ventricular blanking period (VBP), and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any A-V delay, and an atrial blanking period (ABP) during which atrial sensing is disabled. It should be noted that the starting of the post-atrial time periods and the A-V delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates A-V delays, post-ventricular time periods, and post-atrial time periods that vary with the sensor-based escape interval established in response to the RCP(s) and/or with the intrinsic atrial and/or ventricular rate.

The output amplifiers circuit 51 contains a RA pace pulse generator (and a LA pace pulse generator if LA pacing is provided), a RV pace pulse generator, a LV pace pulse generator, and/or any other pulse generator configured to provide atrial and ventricular pacing. In order to trigger generation of an RV-PACE or LV-PACE pulse, digital controller/timer circuit 43.

The output amplifiers circuit 51 includes switching circuits for coupling selected pace electrode pairs from among the lead conductors and the IND-CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 43 controls sensitivity settings of the atrial and ventricular sense amplifiers 55.

The sense amplifiers may be uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV, and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 43. Similarly, left atrial depolarizations or P-waves in the LA-SENSE signal that are sensed by the LA sense amplifier, if provided, result in a LA-EVENT signal that is communicated to the digital controller/timer circuit 43. Ventricular depolarizations or R-waves in the RV-SENSE signal are sensed by a ventricular sense amplifier result in an RV-EVENT signal that is communicated to the digital controller/timer circuit 43. Similarly, ventricular depolarizations or R-waves in the LV-SENSE signal are sensed by a ventricular sense amplifier result in an LV-EVENT signal that is communicated to the digital controller/timer circuit 43. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

The techniques described in this disclosure, including those attributed to the IMD 16 and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

The illustrative systems, devices, and rate responsive pacing methods may be used to provide evaluation of a patient's cardiac health and/or evaluation and configuration of cardiac therapy being delivered to the patient. For example, the illustrative systems, devices, and rate responsive pacing methods may be used to determine and adjust a rate responsive pacing profile, as described further herein, based on activity information monitored over time.

Figure 4:
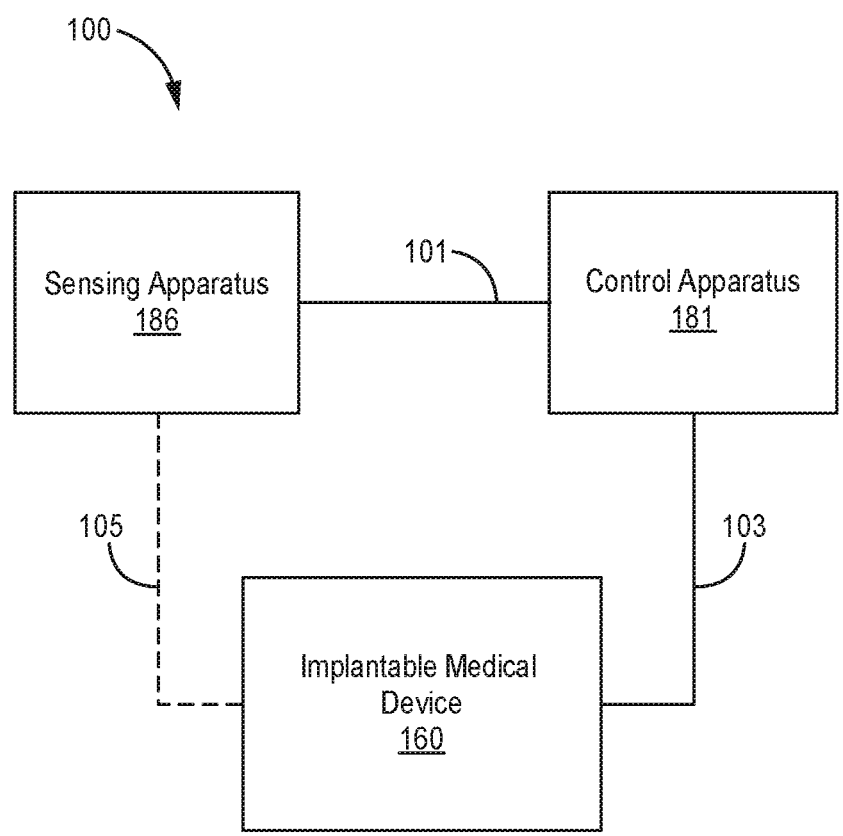
FIG. 4 is an illustrative block diagram of a therapy system for delivering cardiac therapy in accordance with aspects of the present disclosure.

FIG. 4 is an illustrative block diagram of a therapy system 100 for delivering cardiac therapy in accordance with aspects of the present disclosure. The therapy system 100 can be a rate responsive pacing system for delivering RRP to a patient. The therapy system 100 includes a sensing apparatus 186, a control apparatus 181, and an implantable medical device 160 (IMD). The sensing apparatus 186, the control apparatus 181, and the implantable medical device 160 are similar to, and include features akin to, those discussed above with respect to the sensing apparatus 86, the control apparatus 81, and the implantable medical device 60. For example, the sensing apparatus 186 may include one or more sensors (e.g., configured to sense a patient's activity to provide activity info and activity levels), the control apparatus 181 includes processing circuitry, and the implantable medical device 160 (or electrode apparatus) includes a plurality of pacing electrodes, as similarly discussed above with respect to FIG. 3B. The control apparatus 181 is operably coupled to the sensing apparatus 186 and the implantable medical device 160 is operably coupled to the control apparatus 181 as indicated by lines 101 and 103, respectively. In one example, the sensing apparatus 186 can be operably coupled to the implantable medical device, as indicated with the dashed line 105.

It is to be understood that the control apparatus 181 and the sensing apparatus 186, and similarly, the control apparatus 181 and the implantable medical device 160, may be operatively coupled to each other in a plurality of different ways so as to perform, or execute, the functionality described herein. For example, the control apparatus 181 may be wirelessly operably coupled to the sensing apparatus 186 as depicted by the line 101 extending therebetween. In one example, one or both of the sensing apparatus 186 and the control apparatus 181 can be included within the implantable medical device 160. In one example, the control apparatus 181 is included in a remote computing device (not shown) that may be operably coupled (e.g., wirelessly) to the sensing apparatus 186 and the implantable medical device 160.

The sensing apparatus 186 is employed to sense and collect activity information related to, or based on, the patient's physiological response of the patient's body indicative of movement, such as exercise. The sensing apparatus 186 includes a sensor to sense activity information of a patient. For example, the sensing apparatus 186 may be configured to sense an increase or decrease in the patient's physical activity. The sensing apparatus 186 can include one or more than one sensor or type of sensors. The sensing apparatus 186 can sense, for example, at least one of patient movement information, pulse wave velocity signals, electrocardiogram signals, intracardiac electrogram signals, blood pressure measurement, transthoracic impedance, subcutaneous impedance, temperature, heart sounds, and perfusion level. Perfusion level, for example, is can be a measurement of the 02 content in the patient's tissues sensed with an optical sensor. Other types of sensed activity information of the patient by the sensor may also be used.

The control apparatus 181 can receive the sensed activity information from the sensing apparatus 186. In one example, the control apparatus 181 can monitor and store sensed activity information of the patient received from the sensing apparatus 186. The control apparatus 181 can determine a rate responsive pacing (RRP) profile (see, e.g., FIG. 5) to be provided to the implantable medical device 160 based on the sensed activity information received from the sensing apparatus 186, as further described below.

The control apparatus 181 can determine and provide RRP profiles to the implantable medical device 160 based on sensed activity information from the sensing apparatus 186. The implantable medical device 160 delivers cardiac pacing (i.e., rate responsive pacing) to the patient at a pacing rate corresponding to the RRP profile determined by the control apparatus 181. For example, the RRP profile may increase the patient's paced heart rate based on an increase in activity level, or no change in the activity level, and may decrease the patient's paced heart rate based on an undesirable patient condition. In one example, the pacing is selectively delivered during periods or durations of increased patient activity indicated by ongoing or periodically sensed activity information and is not delivered during periods or durations of rest indicated by a sensed resting heart rate. An increased activity level indicated by increased bodily movement of the patient for a period of time (e.g., 1-5 minutes) can indicate an activity event during which RRP is to be initiated. For example, an activity event can include a patient walking at a slow to brisk pace, as measured by an accelerometer as approximately 70-100 accelerometer counts over a one minute duration, translating to a walking speed of approximately one mile/hour. In one example, delivering RRP to the patient at the pacing rate corresponding to the RRP profile occurs when the sensed and monitored activity information is indicative of the activity level of the patient above a predetermined minimum that indicates an activity event. During therapy, the RRP profile can be adjusted based on additionally sensed activity information. In one example, the defined time period that a particular RRP profile is enabled can be sufficient for remodeling of the heart to occur, indicated by improved cardiac output or tissue perfusion. The control apparatus 181 can select and provide adjusted RRP profiles to the implantable medical device 160 based on sensed activity information from the sensing apparatus 186, as further described below.

Figure 5:
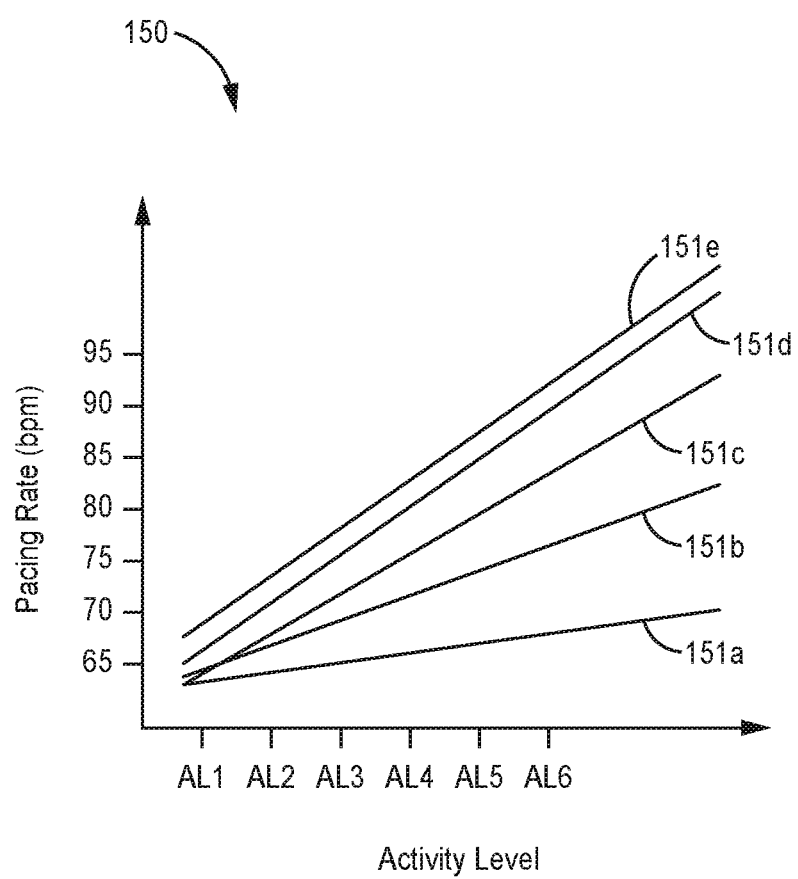
FIG. 5 is a graphical representation of some example RRP profiles useful in a cardiac therapy system in accordance with aspects of the present disclosure.

FIG. 5 is a graphical representation of some example RRP profiles useful in a cardiac therapy system in accordance with aspects of the present disclosure. A plurality of rate responsive profiles, such as the profiles indicated with lines 151a-151e, can be determined by the control apparatus 181 of FIG. 4, for example. The plurality of RRP profiles 151a-151e are representative only, and additional and/or other RRP profiles are understood to be within the scope of the present disclosure. Although illustrated linearly, any or all of the RRP profiles 151a-151e can be stepped, curved, or any other shape or function. In one example, the RRP profiles increases steadily and then the increase may begin to taper where the HR saturates to an age adjusted maximal HR (i.e., 220 bpm—age). Maximal allowed HR may be lower if the patient on medication such as beta-blockers or $I_f$ channel blockers (e.g. ivabradine). In some examples, RRP profiles can be tailored for each individual patient depending on their health status, medication usage, demographics (e.g., age, gender etc.) and lifestyle. In some examples, the RRP profiles can be automatically updated (e.g. every six months or a year) and adjusted in accordance with the changing health status of the patient. Regardless, the RRP profiles 151a-151e include adjustments to the pacing rate such that the pacing rate is adjusted corresponding to the activity level of the patient based at least partially on the sensed activity information received by the control apparatus from the sensing apparatus (see also, e.g., FIG. 4).

With continued reference to FIG. 5, in one example, the RRP profiles 151a-151e are each formed of pacing rates that increase as the patient's activity level increases. The RRP profile may be described as providing, or generating, a pacing rate based on the patient's activity level. In other words, the RRP profile may be described as pacing rate as a function of an activity level. In one example, the RRP profiles can be programmed into and/or developed by the control apparatus 181. Each of the plurality of RRP profiles can include or generate a pacing rate that is increased as the activity level of the patient increases. The pacing rates can be aggressively increased, to increase the pacing rate to a higher pacing rate more quickly, indicated by a sharp increase in the slope of RRP profile line (e.g., 151*c*), or can be less aggressively increased, to increase the pacing rate to a smaller rate, indicated by a lesser slope of the RRP profile line (e.g., 151*a*). The RRP profiles can be progressively scaled (e.g., increased) in terms of aggressiveness, with a more aggressive RRP profile having a greater increase in pacing rate over a determined activity level increase than a less aggressive RRP profile. For example, RRP 151*b* increases more gradually over an increase in activity level from low level, AL1, to a moderate level, AL3 than RRP 151*d* over the same increase in activity level, AL1 to AL3, as indicated in FIG. 5. The applied profiles could be increased, for example, from the less aggressive RRP profile 151*a* to the more aggressive RRP profile 151*e* over time, if there are no undesirable patient conditions present in the patient, as discussed further below with respect to FIGS. 6 and 7.

Figure 6:
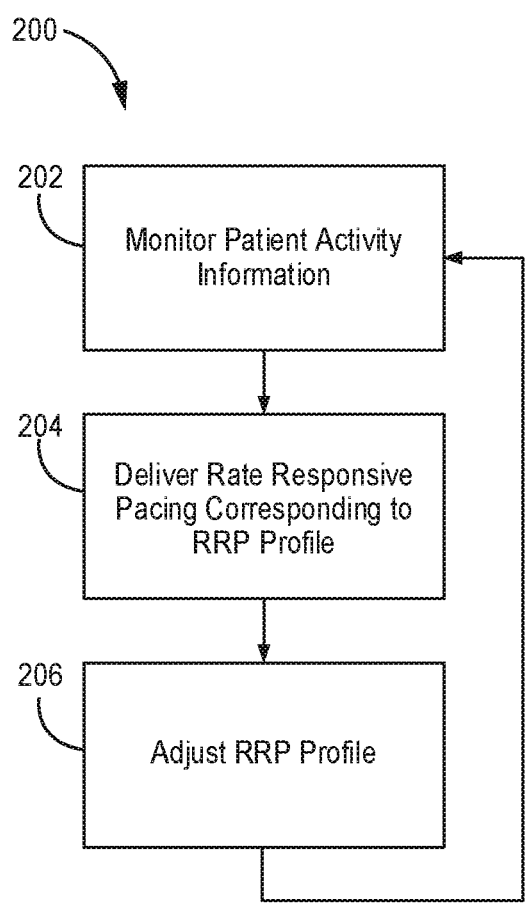
FIG. 6 illustrates an example method of delivering RRP therapy in accordance with aspects of the present disclosure.

FIG. 6 illustrates an example method 200 of delivering RRP therapy in accordance with aspects of the present disclosure. The illustrative method 200 may include monitoring activity information related to an activity level of a patient at 202. At 202, monitoring activity information can include measuring, recording, and storing activity information of the patient, for example. The monitored activity information can be related to, or based on, the patient's physiological response of the patient's body indicative of movement or activity, such as exercise. The monitored activity information can include patient movement information including pulse wave velocity signals, electrocardiogram signals, intracardiac electrogram signals, blood pressure measurement, transthoracic impedance, subcutaneous impedance, temperature, heart sounds, and perfusion level, for example. The monitored activity information can be indicative of the current and past metabolic demand of the patient useful to determine adjustments to the RRP profile by the control apparatus.

After the monitoring 202 of the activity information (e.g., for a determined time period such as two weeks), the illustrative method 200 may initiate the delivery of RRP corresponding to a RRP profile at 204. For example, one of the RRP profiles 151*a-e* illustrated in FIG. 5 can be employed. The delivery 204 of RRP corresponding to the selected RRP profile can be applied with the medical device (e.g., IMD 160) implanted into a patient to deliver the RRP therapy to the heart. In some examples, the IMD may deliver pacing pulses in accordance with one, or more than one, of the available RRP profiles over the course of the RRP therapy.

The method 200 may include adjusting the RRP profile 206 by evaluating the patient's activity information monitored one or both of before and during RRP 204. Adjusting 206 or changing to a different RRP profile of the plurality of profiles delivered to the IMD may occur during, or simultaneous with, the monitoring 202 of the activity information of the patient over a duration of time after the delivery of RRP corresponding to a first, or initial, RRP profile. For example, the RRP may be initially delivered at a pacing rate corresponding to the RRP profile 151*a* and adjusted to one of the other RRP 151*b*-151*e* illustrated in FIG. 5 at a later time based on the sensed and monitored activity information of the patient. In some examples, perfusion level, blood pressure, temperature, and/or other activity information of the patient can be sensed in parallel with one another during the RRP therapy 200. The RRP therapy 200 of the patient can automatically monitor, deliver, and adjust of the RRP profiles at 202-206 which may be described as a closed-loop RRP therapy.

During, or simultaneous with, the delivery of RRP corresponding to the initially or currently delivered RRP profile at 204, upcoming or future adjustment to the RRP are evaluated and determined at 206. With the adjusting of the RRP profile at 206, the activity information of the patient can concurrently, or subsequently, be monitored at 202. If the monitored activity information at 202 indicates a change in the patient's activity level over time, then the control apparatus may determine that a different RRP profile (then the RRP profile currently delivered) is more suitable to deliver RRP at a suitable pacing rate for the patient via the IMD, and the RRP profile is adjusted at 206 accordingly.

The implantable medical device (e.g., electrode apparatus) can deliver cardiac pacing at pacing rates corresponding to each of the determined or generated RRP profiles. The RRP profile can be adjusted from a first RRP profile of a plurality of RRP profiles to a second RRP profile of the plurality of RRP profiles based on the sensed activity information indicating an increase in an activity level of the patient. The pacing electrodes can deliver cardiac pacing at the pacing rate corresponding to the RRP profile during activity events based on the sensed activity information. In one example, adjusting the RRP profile based on the monitored activity information includes periodically adjusting the RRP profile based on the monitored activity information after a time period, wherein the time period is greater than one day. In one example, adjusting the RRP profile based on the monitored activity information includes decreasing aggressiveness of the RRP profile in response to the monitored activity information indicating one or more undesirable patient conditions.

Figure 7:
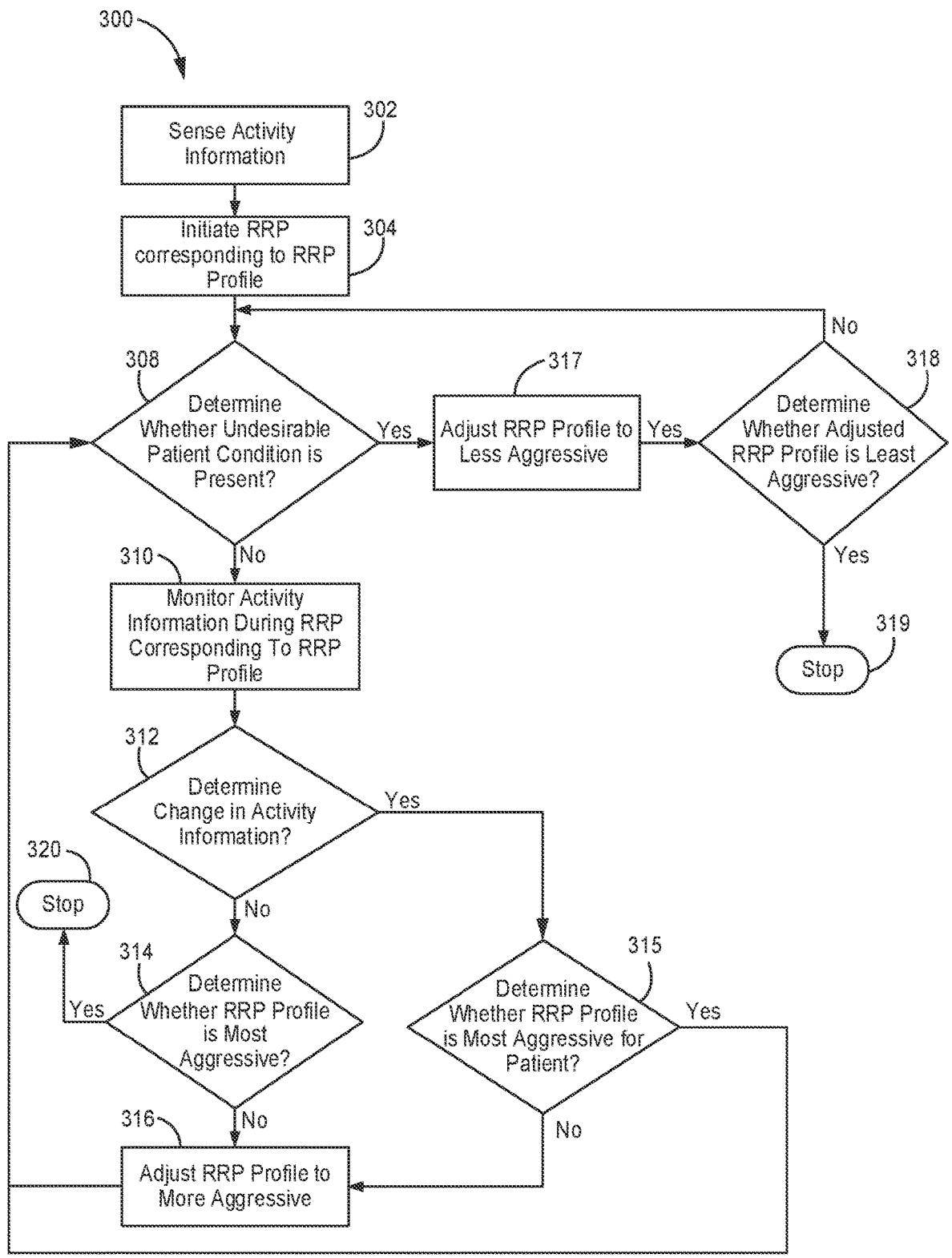
FIG. 7 illustrates another example method of delivering RRP therapy in accordance with aspects of the present disclosure.

FIG. 7 illustrates a flow diagram of a method 300 of delivering rate responsive pacing therapy to a patient in accordance with aspects of the present disclosure. According to the illustrative example of method 300, activity information of a patient is sensed at 302 during a time period (e.g., two weeks). In one example, during the sensing of the activity information at 302, pacing is not delivered to the patient during the duration of the time period. The sensed activity information can provide a baseline of the patient's condition and activity level that can be useful in determining the RRP profile(s) to be applied during therapy. The sensed activity information related to the patient activity may include any sensed patient movement information including, but not limited to, pulse wave velocity signals, electrocardiogram signals, intracardiac electrogram signals, blood pressure measurement, and perfusion level.

In one example, the activity information is sensed, or acquired, by the sensing apparatus over a first defined time period, or first duration of time. The first defined time period can be hours, days, or weeks. For example, the defined time period can be selected to be greater than one day. The defined time period can be patient specific. Factors in determining the length, or duration, of the defined time period can include patient specific factors such as age, gender, lifestyle etc. and also baseline health status of the patient which can be either be qualitatively assessed (e.g. number of comorbidities) or quantitatively assessed (e.g. by doing a standard frailty assessment). Also, a device-based criterion can be used (e.g. 10,000 cumulative accelerometer counts) and duration in that case is adjusted automatically based on the patient's health status and lifestyle as an example. In one example, the activity information includes a first, or initial, activity information related to a first activity level of the patient that is sensed by the sensing apparatus during the first, or initial, time period and determined by the control apparatus prior to delivering rate responsive pacing to the patient's heart with the implantable medical device. The first activity information can be used to establish a baseline of activity information of the patient prior to initiating pacing. The first, or baseline, activity information can be useful in determining an appropriate RRP profile to use with the initial RRP therapy. The first activity information, as well as subsequently monitored activity information, can be stored for reference and further determination of suitable RRP profiles to be employed in providing RRP to the patient during various phases of the therapy.

After the baseline activity information is sensed at 302, an implanted medical device can initiate RRP corresponding to a RRP profile at 304. In one example, the initiated RRP corresponds to an initial RRP profile determined based on the sensed activity information at 302. In one example, the initiated RRP can be delivered at a pacing rate that is a slightly increased over the patient's pre-pacing, or base, heart rate. For example, initial pacing rate corresponding to the RRP profile delivered to the patient can be a percentage or a determined beats per minute increase over the base, or pre-paced, heart rate of the patient.

The illustrative method 300 may decrease the aggressiveness of the RRP due to, e.g., an undesirable patient condition. Thus, during RRP therapy, the patient may be monitored to determine whether an undesirable patient condition exists at 308. An undesirable patient condition can indicate an adverse health state or condition. For example, the ST segment (from a sensed electrogram) may be monitored for ST elevation, and if the ST segment indicates ST elevation, then it may be determined that the patient has an undesirable patient condition. Further, for example, blood pressure may be monitored, and if blood pressure becomes too high or too low, then it may be determined that the patient has an undesirable patient condition. Further, for example, perfusion may be monitored, and if perfusion indicates that patient's blood oxygen saturation has dropped below a certain threshold (e.g. 75%) or greater than certain percentage from baseline (e.g. 15%), then it may be determined that the patient has an undesirable patient condition. Still further, for example, the patient may have one or more symptoms that may be undesirable such as, e.g., dyspnea/shortness of breath and/or increase in breathing rate as measured by device's impedance/EGM based respiration sensor ST segment elevation, abnormal/aperiodic breathing pattern, abnormal decrease or increase in temperature, abnormal increase or decrease in device measured transthoracic impedance, appearance of abnormal heart sounds (e.g. S3 ad S4 heart sounds), which may be suggestive of abnormal fluid shifts/accumulation, onset of atrial arrhythmias, increase in PVC burden, etc., and such symptoms may be acquired to manual entry (e.g., patient input). If such symptoms are undesirable, then it may be determined that the patient has an undesirable effect from the RRP related elevation in heart rate resulting in an undesirable patient condition. In one example, the control apparatus can determine the occurrence of an undesirable condition at 308 using, or based on, the sensed activity information of the patient that is being sensed by the sensing apparatus at 302.

In response to the determination at 308 that an undesirable patient condition is present, the illustrative method 300 may adjust the RRP profile at 317 to a new RRP profile that is less aggressive then the RRP profile initially applied (see, e.g., RRP profiles 151a-e illustrated in FIG. 4). For example, the new RRP profile may provide lower pacing rates at similar activity levels than the previously-used RRP profile. Thus, in other words, the patient's heart will not be paced as rapidly, or quickly, has previously paced at the same activity levels to, e.g., reduce or eliminate the previously-determined undesirable patient conditions at 308.

Additionally, if the RRP profile was already the least aggressive at 318 as provided by the method 300, then the method 300 may stop, e.g., so as to cease any further adjustment to the RRP profile. More specifically, after the adjustment to the RRP profile at 317, the method 300 may determine whether the adjusted RRP profile is at the lowest level or is the least aggressive RRP profile available at 318. In response to determining that the applied RRP profile is least aggressive, further adjustments to the RRP profile are stopped at 319. Alternatively, if the RRP profile being applied is not the least aggressive, the patient may be again be monitored to determine whether an undesirable patient condition exists at 308. If the patient experiences an undesirable patient condition at the least aggressive RRP profile, the RRP therapy may be stopped for a duration (e.g., one week, two weeks, a month, etc.) and then re-initiated in further attempts to assist the patient with the RRP therapy.

In response to a determination that an undesirable patient condition is not present at 308, activity information is monitored during delivery of RRP corresponding to the RRP profile at 310. In one example, the monitored activity information may include any of the sensed patient movement information discussed above with respect to the sensed activity information at 302. For example, the monitored activity information can relate to sensed patient information including, but not limited to, accelerometer signals, pulse wave velocity signals, electrocardiogram signals, intracardiac electrogram signals, blood pressure measurement, and perfusion level.

For example, the control apparatus can monitor a second sensed activity information related to a second activity level of the patient during RRP corresponding to the initial RRP profile. The second activity information is determined with sensed information acquired by the sensing apparatus over a second time period. The second time period can be of an equal length of time, or a different length of time, then the first time period. Similarly, as the therapy 300 continues, subsequent, or additional, activity information and/or subsequent, or additional, time periods can also be sensed and monitored and the first and second activity information and time periods are merely illustrative and not to be viewed as limiting.

After receiving the sensed and monitored activity information of the patient, a change to the activity information can be determined at 312. For example, the method 300 may determine whether the patient's activity level has increased, decreased, or remained the same. In one example, change in the activity information at 312 can include comparing the sensed activity information of 302 (e.g., first activity information) to the monitored activity information during RRP corresponding to the RRP profile of 310 (e.g., second activity information). In other words, the control apparatus can compare activity information related to the patient's activity levels over the first and second defined time periods. For example, activity information such as accelerometer rates can be sensed and stored during each of the time periods, respectively, and the highs, lows and/or averages can be compared. The compared activity information can be useful in assessing the suitability of the RRP profile applied to the patient. For example, an increase in the patient's activity level indicated by the activity information can be indicative of improvement to the patient's cardiac health.

The illustrative method 300 can use changes in the activity information to determine whether the selected (e.g., applied) RRP profile is the most aggressive RRP profile by the system and/or provided for the specific patient receiving RRP therapy. For example, the RRP profile can be increased the most aggressive RRP profile (e.g., 151e of FIG. 5) but will not exceed the maximal heart rate for the patient (i.e., 220 minus age). In some examples, the pacing applied at the most aggressive RRP profile will be 10%-20% below the maximal heart rate for the patient. In response to a change in the patient's activity information (e.g., increase in accelerometer rate) determined at 312, the method accesses whether the applied RRP profile is the most aggressive for the patient at 315. It can be desirable to apply the most aggressive RRP profile for the patient to provide heart rate pacing to the patient at in order to maximize the heart functionality of the patient. In response to a determination that the RRP profile is the most aggressive for the patient at 315, the method 300 may return to monitoring whether an undesirable patient condition exists at 308.

In response to a determination that the RRP profile being applied is not the most aggressive available for the patient at 315, the illustrative method 300 may adjust the RRP profile at 316 to a new RRP profile that is more aggressive then the RRP profile currently, or previously, being applied (see, e.g., RRP profiles 151a-e illustrated in FIG. 5). For example, an adjusted RRP profile can be selected that is more aggressive than the RRP profile being currently provided in response to the determination that the RRP profile being applied to the patient is not the most aggressive that can be applied to the patient having an increase in activity level. The control apparatus can adjust the RRP profile until a maximum, or most, aggressiveness RRP profile is determined at 315. For example, the adjusted RRP profile may provide higher pacing rates at similar activity levels than the previously applied RRP profile. In this manner, the patient's heart can be paced more rapidly, or quickly, than previously paced at the same activity levels. After the RRP profile is adjusted to a more aggressive RRP profile at 316, the patient may again, or continue to, be monitored to determine whether an undesirable patient condition exists during pacing of the patient's heart at the more aggressive RRP profile at 308.

In some examples, no change to the monitored activity information of the patient is determined to have occurred over the defined time period at 312. In response to the determination of no change to the activity information of the patient at 312, a determination can be made as to whether the most aggressive RRP profile has been applied at 314. In one example, if the method 300 determines at 314 that the most aggressive RRP profile has not been applied, the RRP profile may be adjusted to a more aggressive RRP profile. For example, further adjustment to increased pacing rates corresponding to the adjusted RRP profile may be useful to increase blood flow through the heart. After the RRP profile is adjusted to a more aggressive RRP profile at 316, the patient may again, or continue to, be monitored to determine whether an undesirable patient condition exists during pacing of the patient's heart at the more aggressive RRP profile at 308

In other examples, after determining that there is no change in activity information at 312, the method 300 can determine that the most aggressive RRP profile is applied to the patient at 314. As a result, the method 300 may stop, or cease, any further adjustment to the RRP profile at 320. In some examples, further adjustments to the RRP profile will be reassessed with the RRP therapy techniques after a period of time (e.g., one week to one month).

As indicated above and with reference to the method 300 of FIG. 7, the pacing rate can be evaluated and increased corresponding one or more of the plurality of RRP profiles over multiple defined periods, as determined by the control apparatus based on the activity information of the patient and other determinations. In other words, the method 300 can be a closed-loop method that delivers adjusted RRP profiles to the IMD based on the sensed and monitored information. In one example, the method 300 can be employed to gradually transition the patient to higher pacing rates corresponding to a more aggressive RRP profile. The method 300 can adjust to a more or less aggressive RRP profile, or maintain the already selected and applied RRP profile, in accordance to the aggressiveness determinations and the presence of undesirable patient condition(s).

In one example, the method can include providing a plurality of RRP profiles ranging from a least aggressive RRP profile to a most aggressive RRP profile. In one example, adjusting the RRP profile can include selecting one of the plurality of RRP profiles based on the monitored activity information. In one example, adjusting the RRP profile based on the monitored activity information can include increasing aggressiveness of the RRP profile in response to the monitored activity information indicating an increase in the activity level of the patient. In one example, adjusting the RRP profile based on the monitored activity information can include increasing aggressiveness of the RRP profile to a maximum aggressiveness RRP profile. In one example, adjusting the RRP profile based on the monitored activity information can include increasing aggressiveness of the RRP profile in response to the monitored activity information indicating a lack of increase in the activity level of the patient.

The method 300 can include multiple RRP profile adjustments that can be aggregated over multiple steps 302-320 occurring over multiple durations until the least or most aggressive RRP profile is determined for the patient. The control apparatus continues to provide adjusted RRP profiles to the implantable medical device based on continued sensed activity information from the sensing apparatus. The control apparatus can determine and provide one or more RRP profiles (see, e.g., FIG. 5) to the implantable medical device for RRP of the patient during the course (e.g., weeks, months, years) of the therapy including a plurality of defined time periods. Additional determinations and monitoring are continued until the control apparatus determines that either the least or most aggressive RRP profile for that patient is being applied, and further adjustments are stopped at 319 or 320 as described above. In one or more examples, the rate responsive pacing therapy may produce cardiac remodeling in the patient. In some examples, the illustrative method 300 may continue determining and adjusting the RRP profile being applied to cause, and during, remodeling of the heart.

Although the present disclosure has been described with reference to preferred embodiments, workers skilled in the art will recognize that changes can be made in form and detail without departing from the spirit and scope of the present disclosure.

EMBODIMENTS

Embodiment 1: A method of delivering rate responsive pacing therapy comprising:
monitoring activity information related to an activity level of a patient;
delivering a rate responsive pacing (RRP) to the patient at a pacing rate corresponding to a RRP profile, wherein the RRP profile generates the pacing rate based on the activity information; and
adjusting the RRP profile based on the monitored activity information.

Embodiment 2: The method as set forth in embodiment 1, further comprising:
providing a plurality of RRP profiles ranging from a least aggressive RRP profile to a most aggressive RRP profile,
wherein adjusting the RRP profile comprises selecting one of the plurality of RRP profiles based on the monitored activity information.

Embodiment 3: The method as set forth in one of embodiments 1-2, wherein adjusting the RRP profile based on the monitored activity information comprises increasing aggressiveness of the RRP profile in response to the monitored activity information indicating an increase in the activity level of the patient.

Embodiment 4: The method as set forth in embodiment 3, wherein adjusting the RRP profile based on the monitored activity information comprises increasing aggressiveness of the RRP profile to a maximum aggressiveness RRP profile.

Embodiment 5: The method as set forth in one of embodiments 1-4, wherein adjusting the RRP profile based on the monitored activity information comprises increasing aggressiveness of the RRP profile in response to the monitored activity information indicating a lack of increase in the activity level of the patient.

Embodiment 6: The method as set forth in one of embodiments 1-5, wherein monitoring activity information comprises:
determining a first monitored activity information prior to delivering the rate responsive pacing, and
determining a second monitored activity information after delivering the rate responsive pacing,
wherein adjusting the RRP profile based on the monitored activity information comprises comparing the first monitored activity information to the second monitored activity information.

Embodiment 7: The method as set forth in one of embodiments 1-6, wherein delivering RRP to the patient at the pacing rate corresponding to the RRP profile occurs when the monitored activity information is indicative of the activity level of the patient is above a minimum.

Embodiment 8: The method as set forth in one of embodiments 1-7, wherein adjusting the RRP profile based on the monitored activity information comprises periodically adjusting the RRP profile based on the monitored activity information after a time period, wherein the time period is greater than one day.

Embodiment 9: The method as set forth in one of embodiments 1-8, wherein the monitored activity information comprises at least one of patient movement information, pulse wave velocity signals, electrocardiogram signals, intracardiac electrogram signals, blood pressure measurement, transthoracic impedance, subcutaneous impedance, temperature, heart sounds, and perfusion level.

Embodiment 10: The method as set forth in one of embodiments 1-9, wherein adjusting the RRP profile based on the monitored activity information comprises decreasing aggressiveness of the RRP profile in response to the monitored activity information indicating an undesirable patient condition.

Embodiment 11: An implantable medical device comprising;
a sensing apparatus comprising a sensor to sense activity information of a patient;
a control apparatus comprising processing circuitry to select a rate responsive pacing (RRP) profile based on the sensed activity information received from the sensing apparatus; and
an electrode apparatus comprising a plurality of pacing electrodes, the electrode apparatus operably coupled to the control apparatus, the electrode apparatus to deliver rate responsive pacing to the patient at a pacing rate corresponding to the RRP profile,
wherein control apparatus is to adjust the RRP profile based on the sensed activity information.

Embodiment 12: The device as set forth in embodiment 11, wherein the pacing electrodes are to deliver rate responsive pacing at the pacing rate corresponding to the RRP profile during activity events based on the sensed activity information.

Embodiment 13: The device as set forth in one of embodiments 11-12, wherein the control apparatus is to adjust the RRP profile based on the sensed activity information indicating an increase in the patient's activity and a maximum aggressiveness is not exceeded.

Embodiment 14: The device as set forth in one of embodiments 11-13, wherein the electrode apparatus is to deliver rate responsive pacing corresponding to a plurality of RRP profiles, wherein the RRP profile is adjusted from a first RRP profile of a plurality of RRP profiles to a second RRP profile of the plurality of RRP profiles based on the sensed activity information indicating an increase in an activity level of the patient.

Embodiment 15: A therapy system comprising:
a sensing apparatus comprising a sensor to sense activity information of a patient;
a control apparatus comprising processing circuitry, the control apparatus operably coupled to the sensing apparatus, the control apparatus configured to:
monitor sensed activity information of the patient,
determine a first activity information of a patient related to a first activity level of the patient,
determine a second activity information related to a second activity level of the patient,
compare the first activity information to the second activity information, and
determine a rate responsive pacing (RRP) profile based on the compared activity information; and
an implantable medical device comprising pacing electrodes, the implantable medical device operably coupled to the control apparatus, the electrodes to deliver rate responsive pacing (RRP) to the patient at a pacing rate corresponding to the determined RRP profile.

Embodiment 16: The system as set forth in embodiment 15, wherein the control apparatus is to provide adjusted RRP profiles to the implantable medical device based on sensed activity information from the sensing apparatus.

Embodiment 17: The system as set forth in embodiment 16, wherein the control apparatus is to determine a less aggressive RRP profile if the sensed activity information indicates an undesired patient condition, and wherein the pacing rate delivered by the electrodes of the implantable medical device is adjusted to correspond to the less aggressive RRP profile.

Embodiment 18: The system as set forth in one of embodiments 15-17, wherein the control apparatus is to provide an adjusted RRP profile that is more aggressive than the RRP profile to the implantable medical device in response to an increase in an activity level of the patient indicated by the sensed activity information from the sensor apparatus.

Embodiment 19: The system as set forth in one of embodiments 15-18, wherein the sensing apparatus is to sense at least one of patient movement information, pulse wave velocity signals, electrocardiogram signals, intracardiac electrogram signals, blood pressure measurement, transthoracic impedance, subcutaneous impedance, temperature, heart sounds, and perfusion level.

Embodiment 20: The system as set forth in one of embodiments 15-19, wherein the implantable medical device comprises at least one of the control apparatus and the sensing apparatus.

The invention claimed is:

1. An implantable medical device comprising:
   a sensing apparatus comprising a sensor to sense activity information of a patient;
   a control apparatus comprising processing circuitry to select a rate responsive pacing (RRP) profile from a plurality of RRP profiles ranging from a least aggressive RRP profile to a most aggressive RRP profile based on the sensed activity information received from the sensing apparatus, wherein each of the plurality of RRP profiles generates a pacing rate based on the sensed activity information over a same range of sensed activity information; and
   an electrode apparatus comprising a plurality of pacing electrodes, the electrode apparatus operably coupled to the control apparatus, the electrode apparatus to deliver rate responsive pacing to the patient at the pacing rate generated by the selected RRP profile,
   wherein selecting the RRP profile from the plurality of RRP profiles comprises selecting a more aggressive RRP profile from the plurality of RRP profiles than the previously selected RRP profile based on the sensed activity information indicating an increase in the patient's activity and the most aggressive RRP profile of the plurality of profiles is not already selected.

2. The device of claim 1, wherein the pacing electrodes deliver rate responsive pacing at the pacing rate generated by the selected RRP profile during activity events based on the sensed activity information.

3. The device of claim 1, wherein selecting the RRP profile from the plurality of RRP profiles comprises selecting a less aggressive RRP profile from the plurality of RRP profiles than the previously selected RRP profile based on the sensed activity information indicating an undesirable patient condition.

4. A therapy system comprising:
   a sensing apparatus comprising a sensor to sense activity information of a patient;
   a control apparatus comprising processing circuitry, the control apparatus operably coupled to the sensing apparatus, the control apparatus configured to:
      monitor sensed activity information of the patient,
      determine a first activity information of a patient related to a first activity level of the patient,
      determine a second activity information related to a second activity level of the patient,
      compare the first activity information to the second activity information,
      determine a rate responsive pacing (RRP) profile from a plurality of RRP profiles ranging from a least aggressive RRP profile to a most aggressive RRP profile based on the compared activity information, wherein each of the plurality of RRP profiles generates a pacing rate based on the sensed activity information over a same range of sensed activity information, and
      determine a more aggressive RRP profile of the plurality of RRP profiles than the previously determined RRP profile in response to an increase in an activity level of the patient indicated by the sensed activity information from the sensor apparatus; and
   an implantable medical device comprising pacing electrodes, the implantable medical device operably coupled to the control apparatus, the pacing electrodes to deliver rate responsive pacing (RRP) to the patient at the pacing rate generated by the determined RRP profile.

5. The system of claim 4, wherein the control apparatus is further configured to determine a less aggressive RRP profile of the plurality of RRP profiles than the previously determined RRP profile if the sensed activity information indicates an undesired patient condition.

6. The system of claim 4, wherein the sensing apparatus senses one or more of patient movement information, pulse wave velocity signals, electrocardiogram signals, intracardiac electrogram signals, blood pressure measurement, transthoracic impedance, subcutaneous impedance, temperature, heart sounds, and perfusion level.

7. The system of claim 4, wherein the implantable medical device comprises at least one of the control apparatus and the sensing apparatus.

8. A method of delivering rate responsive pacing therapy comprising:
   monitoring activity information related to an activity level of a patient;
   selecting a rate responsive pacing (RRP) profile from a plurality of RRP profiles ranging from a least aggressive RRP profile to a most aggressive RRP profile based on the monitored activity information, wherein each of the plurality of RRP profiles generates a pacing rate based on the sensed activity information over a same range of sensed activity information; and
   delivering a rate responsive pacing (RRP) to the patient at the pacing rate generated by the selected RRP profile, wherein the selected RRP profile generates the pacing rate based on the activity information,
   wherein selecting the RRP profile from the plurality of RRP profiles based on the monitored activity information comprises selecting a more aggressive RRP profile from the plurality of RRP profiles than the previously selected RRP profile in response to the monitored activity information indicating an increase in the activity level of the patient, and the most aggressive RRP profile of the plurality of RRP profiles is not already selected.

9. The method of claim 8, wherein selecting the RRP profile from the plurality of RRP profiles based on the monitored activity information comprises selecting the most aggressive RRP profile from the plurality of RRP profiles.

10. The method of claim 8, wherein monitoring activity information comprises:
    determining a first monitored activity information prior to delivering the rate responsive pacing, and
    determining a second monitored activity information after delivering the rate responsive pacing, wherein selecting the RRP profile from the plurality of RRP profiles based on the monitored activity information comprises comparing the first monitored activity information to the second monitored activity information.

11. The method of claim 8, wherein delivering RRP to the patient at the pacing rate corresponding to the selected RRP profile occurs when the monitored activity information is indicative of the activity level of the patient is above a minimum.

12. The method of claim 8, wherein selecting the RRP profile from the plurality of RRP profiles based on the monitored activity information comprises periodically selecting the RRP profile based on the monitored activity information after a time period, wherein the time period is greater than one day.

13. The method of claim 8, wherein the monitored activity information comprises at least one of patient movement information, pulse wave velocity signals, electrocardiogram signals, intracardiac electrogram signals, blood pressure measurement, transthoracic impedance, subcutaneous impedance, temperature, heart sounds, and perfusion level.

14. The method of claim 8, wherein selecting the RRP profile from the plurality of RRP profiles based on the monitored activity information comprises selecting a less aggressive RRP profile from the plurality of RRP profiles than the previously selected RRP profile in response to the monitored activity information indicating an undesirable patient condition.

15. The device of claim 1, wherein the plurality of RRP profiles are programmed into the control apparatus.

16. The device of claim 1, wherein the plurality of RRP profiles are developed by the control apparatus.

* * * * *